United States Patent [19]
Cabrera et al.

[11] Patent Number: 5,520,608
[45] Date of Patent: May 28, 1996

[54] ORTHOPAEDIC RETRACTOR BLADE

[75] Inventors: Rene J. Cabrera, Stoughton, Mass.;
John R. Bookwalter, Brattleboro, Vt.;
Joseph L. Chaudoin, Wrentham, Mass.

[73] Assignee: Johnson & Johnson Professional, Inc., Raynham, Mass.

[21] Appl. No.: 233,900

[22] Filed: Apr. 28, 1994

[51] Int. Cl.$^6$ ............................ A61B 17/02; A61B 17/56
[52] U.S. Cl. .................... 600/201; 600/210; 600/227; 600/233
[58] Field of Search ................. 128/20; 600/201, 600/210, 208, 227, 233

[56] References Cited

U.S. PATENT DOCUMENTS

| | | | |
|---|---|---|---|
| 2,623,517 | 12/1952 | Barlow et al. | 128/20 |
| 2,695,607 | 11/1954 | Hipps | 128/20 |
| 3,731,673 | 5/1973 | Halloran | 128/20 |
| 3,749,088 | 7/1973 | Gauthier | 128/20 |
| 3,776,240 | 12/1973 | Woodson | 128/20 |
| 4,099,521 | 7/1978 | Nestor et al. | 128/20 |
| 4,747,395 | 5/1988 | Brief | 128/20 |
| 4,813,401 | 3/1989 | Grieshaber | 128/20 |
| 5,000,163 | 3/1991 | Ray et al. | 128/20 |
| 5,303,694 | 4/1994 | Mikhail | 128/20 |

FOREIGN PATENT DOCUMENTS

| | | | |
|---|---|---|---|
| 179309 | 10/1905 | Germany | 128/20 |
| 1333316 | 8/1987 | U.S.S.R. | 128/20 |

OTHER PUBLICATIONS

"A Simple Retractor for Spinal Surgery", G. Mosser Taylor, *Journal of Bone & Joint Surgery*, vol. 28, No. 1, Jan. 1946, pp. 183–184.

Primary Examiner—Richard J. Apley
Assistant Examiner—Kelly McGlashen
Attorney, Agent, or Firm—Michael Q. Tatlow

[57] ABSTRACT

A retractor blade having a generally "S" shaped configuration in cross section. The blade is pivotally attached to a rod which may be connected to a table fixed ring retractor. The central portion of the blade moves tissue away from the operative site when the distal end of the blade is placed against a bone and the rod is moved away from the operative site.

3 Claims, 3 Drawing Sheets

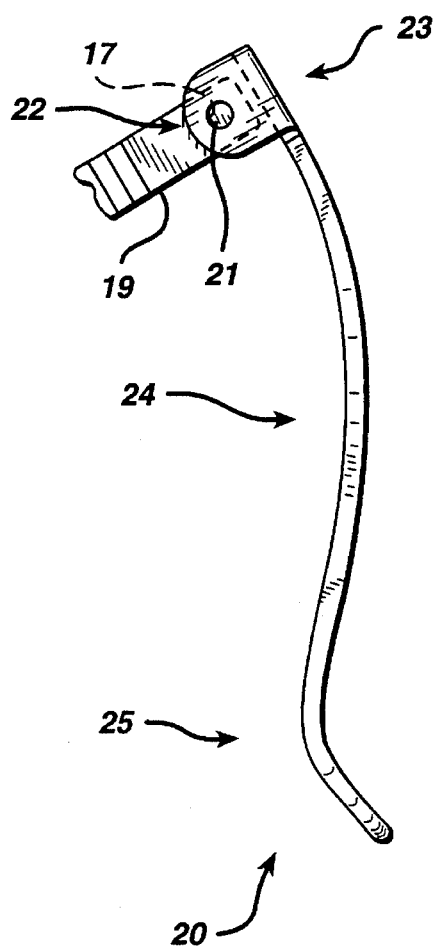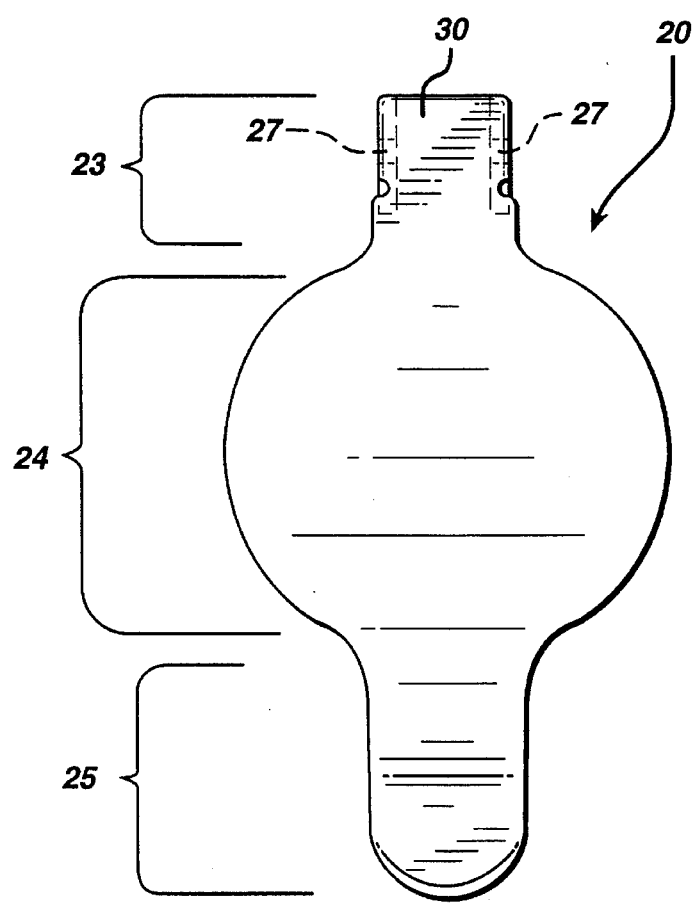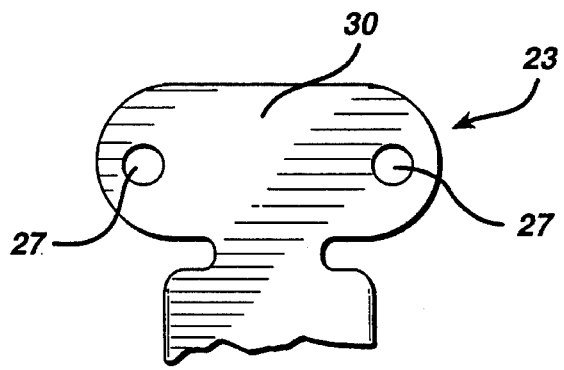

ORTHOPAEDIC RETRACTOR BLADE

BACKGROUND OF THE INVENTION

The present invention relates to a surgical retractor blade used in conjunction with a table fixed retractor system and more particularly is directed to a surgical retractor blade that is particularly advantageous for use in orthopaedic surgery.

In various surgical operations, it is customary to employ surgical retractors. Many such retractors are held in position over the operative site by some type of frame work that is affixed to the operating room table. Some retractor systems employ retractor rings that are positioned over the operative site and the actual retractor blade assemblies are attached to this ring when in use. The retractor blade is applied to the tissue to move it into the desired position and the blade is locked onto the retractor ring so that it is self retained in the proper position during the surgical procedure. These retractors, are generally known as table-fixed surgical retractors. Although the retractor rings find greatest use in abdomen and head surgery, they can also be used in other surgical procedures. Typical variations of this type of retractor are found in U.S. Pat. Nos. 4,934,352; 3,572,326; 2,594,086 and 2,586,488.

The retractor blades themselves have generally flat surfaces which are rigidly affixed to a rod or a bar which in turn is affixed to the retractor ring. To obtain the desired degree of retraction, pressure is exerted on the rod to force the tissue away from the point of the incision and then the rod is secured to the retractor ring. The pressure exerted on the tissue is the force of the blade being held onto the ring. The flat portion of the blade exerts pressure on the tissue to hold it in the desired position out of the operative site and to fully expose the operative site.

The force necessary to move the tissue to expose the operative site with a standard retractor is applied solely by pulling the blade toward the ring or tilting the blade down with a ratchet mechanism which connects the rod to the fixed ring. A ratchet mechanism of this type is disclosed in U.S. Pat. No. 4,424,724. In certain surgical procedures particularly orthopaedic procedures, it is difficult to supply the desired force by pulling the blade in one direction.

SUMMARY OF THE INVENTION

The present invention relates to a retractor blade that is particularly useful in orthopaedic procedures and that is attached to a rod so that the blade can pivot around one end of the rod. The retractor blade has a longitudinal cross sectional configuration which can be characterized as serpentine, sinuous or "S" shaped. The first or proximal end of the retractor blade is pivotally attached to the rod and the second or distal end of the retractor blade can be placed against a bone so that pressure can be applied to pull the blade against adjacent soft tissue. The bone is thus used as a fulcrum to anchor the blade and a prying action instead of a pulling action is used to retract the tissue. This construction allows the surgeon to apply more leverage and therefore more retractive force can be applied than if the only retractive force is applied in the direction along the rod of the retractor. Because the blade is attached to the rod around a pivot, the blade is self adjusting in applying force to the tissue when the force is applied to the rod. Attaching the blade to the rod around a pivot allows the blade to be adjusted through a wide range of motion without detaching the rod from the retractor ring.

The retractor blade of the present invention may have a constant width throughout its length. The preferred embodiment has a relatively narrow portion which is connected to the rod, a second central portion which may be significantly wider than the first portion and a third portion which again is relatively narrow when compared to the second central portion. The third portion is designed to be fitted around or against a bone and to act as a fulcrum when force is applied to the rod. The central portion of the retractor can then exert significant pressure against the tissue to move the tissue to fully expose the operative site.

BRIEF DESCRIPTION OF THE DRAWINGS

FIG. 2 is a side view of a retractor showing the attachment of the blade to the rod.

FIG. 3 is a plan view of the retractor blade of the present invention.

FIG.4 is a partial view of a blank from which the blade of the present invention may be fabricated.

DETAIL DESCRIPTION OF THE INVENTION

Figure 1:
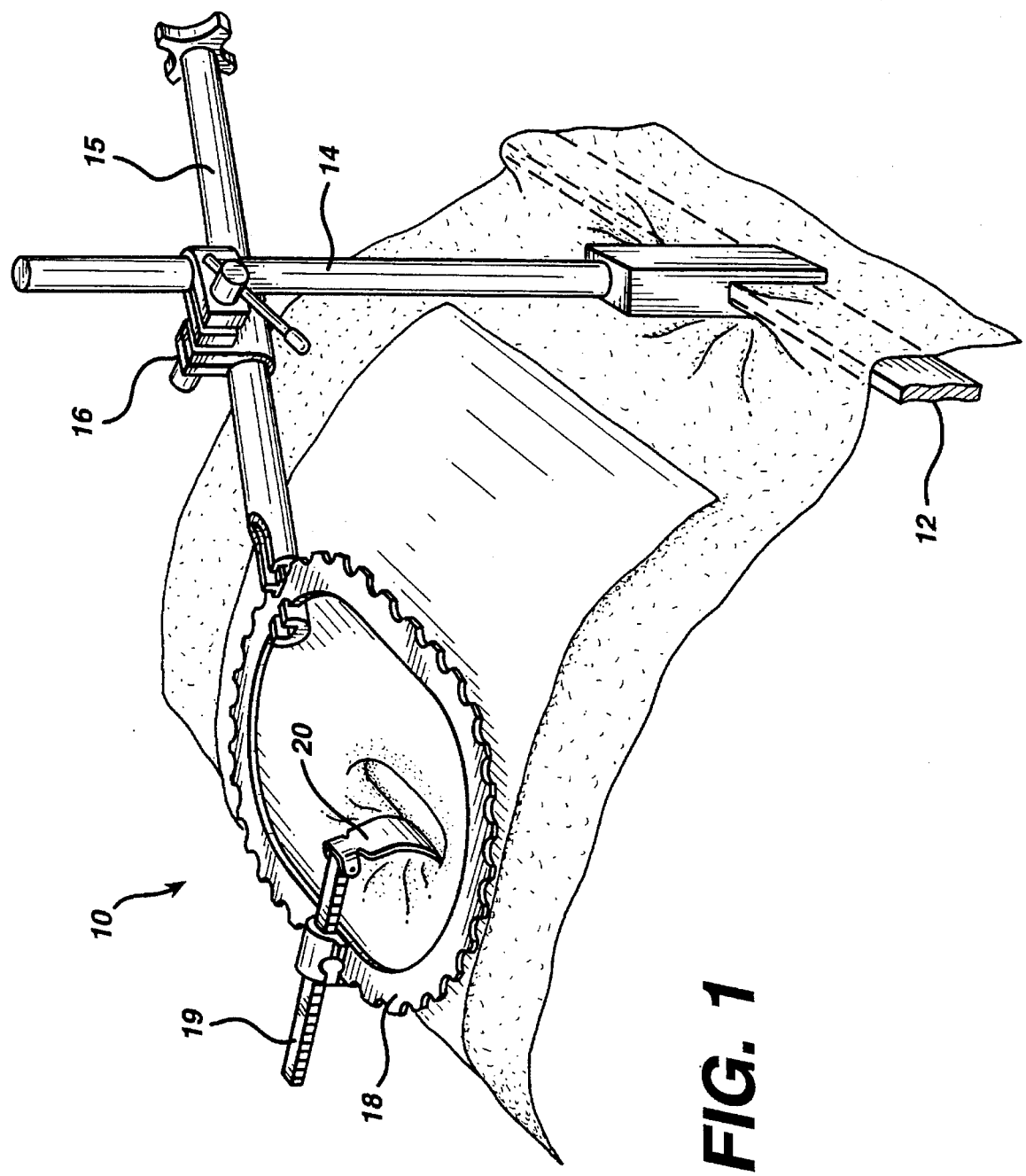
FIG. 1 is a perspective view of a ring type retractor showing the position of the retractor blade in use.

Referring to FIG. 1, there is illustrated a table fixed surgical retractor assembly 10 which is attached to a surgical operating room table 12 in a position so that the retractor ring 18 is positioned over the operative site. The main components supporting the ring are a post 14 and elongate extension rod 15 attached to the post through a clamping mechanism 16. The retractor ring 18 is secured to the end of the extension rod 15. The details of the construction of this device are fully disclosed in U.S. Pat. No. 4,254,763 which is incorporated herein by reference. The retractor itself is composed of a blade 20 which is pivotally attached to the end of rod 19. The rod 19 is secured to the retractor ring 18 by a multi-position ratchet mechanism of the type disclosed in U.S. Pat. No. 4,424,724 or a ratchet mechanism of the type disclosed in U.S. Pat. No. 4,467,791. The retractor blade may have a constant width as shown in FIG. 1, or there may be a variation in the width along the length of the blade. The preferred construction of the retractor blade is best seen in FIGS. 2 and 3. The retractor blade 20 is a generally flat piece of metal which is pivotally attached to the rod 19 with a pin 21 so that the blade can freely rotate around the pin 21 when the rod 19 is moved forward or backward in the ratchet mechanism securing the rod 19 to the retractor ring 18. The pivot pin 21 is aligned perpendicular to the longitudinal axis of the blade and is the axis of the pivoting movement of the blade. The blade has generally three distinct regions, the first region or portion 23 is where the retractor blade is attached to the retractor rod 19. The second central region or portion 24 is a relatively large flat surface which is where the blade will contact the tissue to be displaced in preparation for the surgical procedure. The second portion 25 is between 2 and 4 times greater in width than the first or third portion. The third region or portion 25, is narrower than the width of the second central portion 24 of the retractor blade but preferably wider than the first portion 23 of the blade, up to twice as wide as the first portion. The third portion can be inserted against the bone and when force is applied to the retractor rod 19, the third portion acts a fulcrum against a bone of the patient and the second central portion of the blade exerts force on tissue and moves the tissue away to fully expose the operative site. The proximal end of the blade is the first portion 23 and the third portion 25 of the blade in the distal end of the blade. As shown in FIG. 2, the blade 20 is a curved blade, in which the second portion of the retractor blade curves backward toward the first end of the rod 19 which is the free end of the rod, that is, the portion to which the blade 20 is not attached. The second end 22 of the rod 19 is where the blade is pivotally attached to the rod. The third portion of the blade has a curve which curves toward the second end of the rod and it is this portion of the blade that is anchored to the bone when force is applied to the retractor.

It should be understood that many configurations of blades are possible. The retractor blade shown in FIG. 1 has a constant width along its length and the retractor blade shown in FIG. 3 has a central region that has a greater width than either end. Any blade configuration would be usable if the blade is "S" shaped along its longitudinal axis and is attached to a fixed retractor system through a pivot.

FIG. 4 shows the convenient way to manufacture the end of the retractor blade which is attached to the rod 19. The first portion 23 of the blank from which the blade is made has holes 27 drilled through the attachment end of the blade. The end is bent so that the center section 30 of the end conforms to the width of the end of the retractor rod 19 and the holes 27 will line up with a hole 17 in the rod into which a pin 21 can be affixed to secure the blade to the rod 19. The blank is then bent to form the desired curved shape of the blade. The second portion 24 of the retractor blade should be considerably larger in transverse dimension and in longitudinal dimension, then the first and third portion of the blade. The longitudinal dimension is the length or long axis of the blade and the transverse dimension is on an axis 90 degrees to the longitudinal axis. It is the second portion of the blade that exerts pressure against the tissue and the larger the width, more tissue can be moved out of the way of the operative site.

As indicated above, the central or second portion 24 of the blade is two to four times wider than the first portion 23 of the blade. The central or second portion 24 of the blade has a length that is between about 40 and 60% of the total length of the blade.

Figure 5:
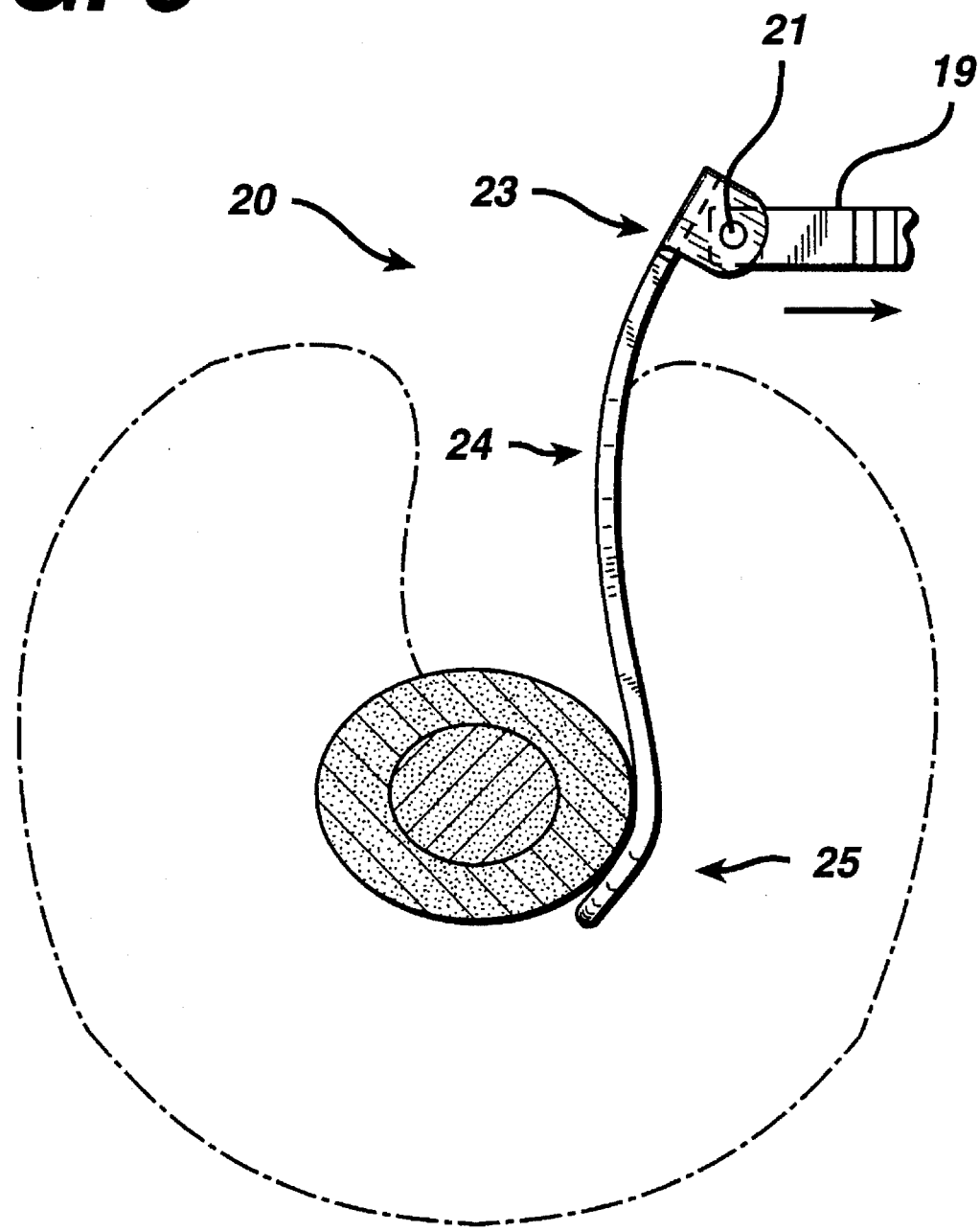
FIG. 5 is a view showing the retractor blade in use prying tissue away from the bone.

FIG. 5 shows the blade in use with the third portion 25 of the blade secured around the bone and the second central portion of the blade 24 displacing the tissue when pressure is applied to the first portion of the blade by moving the rod 19 in the direction of the arrow away from the operative site.

We claim:

1. In a table fixed surgical retractor system comprising an open ring and a tilting ratchet mechanism affixed to the ring, and said ratchet mechanism capable of receiving a retractor assembly, the improvement comprising said retractor assembly comprising an elongated rod having a first end and a second end opposite said first end, said rod adapted to be affixed to the rachet mechanism on the support ring positioned over a surgical patient;

a retractor blade which is "S" shaped along its longitudinal axis and having first, second and third blade portions which are sequentially continuous and which is pivotally attached to the second end of said rod with a pivot pin which is aligned perpendicular to the longitudinal axis of the blade;

said retractor blade having a generally flat tissue contact surface and said first blade portion curved toward the first end of said rod, said second blade portion being at least twice the width of said first blade portion;

said third blade portion curved toward the second end of said rod, said third blade portion being adapted to engage a surface of a bone;

whereby tissue is displaced by said second blade portion when the rod is moved on the support ring in a direction from said second end of the said rod toward said first end of said rod and the retractor blade is free to pivot about said second end of said rod while the rod is being moved to displace the tissue.

2. The surgical retractor of claim 1 in which the length of the second blade portion is 40 to 60% of the total length of the blade.

3. The surgical retractor of claim 2 in which the width of the second blade portion is between 2 and 4 times the width of the first blade portion.

* * * * *